US009295449B2

(12) United States Patent
Zhang et al.

(10) Patent No.: US 9,295,449 B2
(45) Date of Patent: Mar. 29, 2016

(54) LANDMARKS FOR ULTRASOUND IMAGING

(71) Applicant: Ultrasonix Medical Corporation, Richmond (CA)

(72) Inventors: Bill Zhang, Coquitlam (CA); Bo Zhuang, New Westminster (CA); Laurent Pelissier, North Vancouver (CA)

(73) Assignee: Ultrasonix Medical Corporation, Richmond, BC (CA)

( * ) Notice: Subject to any disclaimer, the term of this patent is extended or adjusted under 35 U.S.C. 154(b) by 362 days.

(21) Appl. No.: 13/748,432

(22) Filed: Jan. 23, 2013

(65) Prior Publication Data

US 2013/0211243 A1 Aug. 15, 2013

Related U.S. Application Data

(60) Provisional application No. 61/589,857, filed on Jan. 23, 2012.

(51) Int. Cl.
*A61B 5/00* (2006.01)
*A61B 8/00* (2006.01)
(Continued)

(52) U.S. Cl.
CPC .............. *A61B 8/4263* (2013.01); *A61B 8/0841* (2013.01); *A61B 8/4254* (2013.01); *A61B 8/463* (2013.01); *A61B 10/02* (2013.01); *A61B 10/0233* (2013.01); *A61B 8/14* (2013.01); *A61B 8/469* (2013.01); *A61B 8/5292* (2013.01); *A61B 19/56* (2013.01); *A61B 2017/3413* (2013.01); *A61B 2019/507* (2013.01); *A61B 2019/5276* (2013.01); *A61B 2019/5287* (2013.01)

(58) Field of Classification Search
USPC ......... 600/424, 427, 407, 426, 111, 437, 440; 606/130
See application file for complete search history.

(56) References Cited

U.S. PATENT DOCUMENTS 4,173,228 A 11/1979 Van Steenwyk et al.
4,567,896 A 2/1986 Barnea et al.
(Continued)

FOREIGN PATENT DOCUMENTS

WO 9631753 A2 10/1996
WO 9958055 A1 11/1999
(Continued)

OTHER PUBLICATIONS

Hsu, P-W et al., "Freehand 3D Ultrasound Calibration: A Review", CUED/F-INFENG/TR 584, University of Cambridge Department of Engineering, Dec. 2007.
(Continued)

*Primary Examiner* — John P Leubecker
*Assistant Examiner* — Arnaldo Torres Diaz
(74) *Attorney, Agent, or Firm* — Driggs, Hogg, Daugherty & Del Zoppo, Co. LPA; Anthony M. Del Zoppo, III

(57) ABSTRACT

An ultrasound imaging system has a 3D location system and a data store for recording locations within a patient. Navigation to target locations is facilitated by providing graphical elements superposed on a 2-dimensional image. The size and/or color of the graphical elements are controlled in real time based on distance of the target location(s) from a current image plane. This provides intuitive visual feedback and can be achieved with low computational requirements.

23 Claims, 14 Drawing Sheets

(51) Int. Cl.

| | |
|---|---|
| A61B 10/02 | (2006.01) |
| A61B 8/14 | (2006.01) |
| A61B 8/08 | (2006.01) |
| A61B 17/34 | (2006.01) |
| A61B 19/00 | (2006.01) |

(56) References Cited

U.S. PATENT DOCUMENTS

| | | | |
|---|---|---|---|
| 4,905,698 | A | 3/1990 | Strohl, Jr. et al. |
| 5,078,140 | A | 1/1992 | Kwoh |
| 5,095,910 | A | 3/1992 | Powers |
| 5,211,165 | A | 5/1993 | Dumoulin et al. |
| 5,425,367 | A | 6/1995 | Shapiro et al. |
| 5,443,489 | A | 8/1995 | Ben-Haim |
| 5,515,853 | A | 5/1996 | Smith et al. |
| 5,638,819 | A | 6/1997 | Manwaring |
| 5,647,373 | A | 7/1997 | Paltieli |
| 5,771,896 | A | 6/1998 | Sliwa, Jr. et al. |
| 5,797,849 | A | 8/1998 | Vesely et al. |
| 5,868,675 | A | 2/1999 | Henrion et al. |
| 6,122,538 | A | 9/2000 | Sliwa, Jr. et al. |
| 6,138,495 | A | 10/2000 | Paltieli et al. |
| 6,203,497 | B1 | 3/2001 | Dekel et al. |
| 6,216,027 | B1* | 4/2001 | Willis et al. ............... 600/424 |
| 6,338,716 | B1 | 1/2002 | Hossack et al. |
| 6,459,925 | B1 | 10/2002 | Nields et al. |
| 6,517,491 | B1 | 2/2003 | Thiele et al. |
| 6,524,247 | B2 | 2/2003 | Zhao et al. |
| 6,558,333 | B2 | 5/2003 | Gilboa et al. |
| 6,628,977 | B2 | 9/2003 | Graumann et al. |
| 6,733,458 | B1 | 5/2004 | Steins et al. |
| 6,764,449 | B2 | 7/2004 | Lee et al. |
| 6,875,179 | B2 | 4/2005 | Ferguson et al. |
| 7,142,905 | B2 | 11/2006 | Slayton et al. |
| 7,174,202 | B2 | 2/2007 | Bladen et al. |
| 7,184,991 | B1 | 2/2007 | Wentland et al. |
| 7,244,234 | B2 | 7/2007 | Ridley et al. |
| 7,366,562 | B2 | 4/2008 | Dukesherer et al. |
| 7,383,237 | B2 | 6/2008 | Zhang et al. |
| 7,496,398 | B2 | 2/2009 | Nields et al. |
| 7,510,536 | B2 | 3/2009 | Foley et al. |
| 7,529,393 | B2 | 5/2009 | Peszynski et al. |
| RE40,852 | E | 7/2009 | Martinelli et al. |
| 7,599,730 | B2 | 10/2009 | Hunter et al. |
| RE41,066 | E | 12/2009 | Martinelli et al. |
| 7,751,868 | B2 | 7/2010 | Glossop |
| 8,160,676 | B2* | 4/2012 | Gielen et al. ............... 600/427 |
| 2002/0156376 | A1 | 10/2002 | Wang et al. |
| 2003/0013959 | A1 | 1/2003 | Grunwald et al. |
| 2003/0073895 | A1 | 4/2003 | Nields et al. |
| 2003/0210812 | A1 | 11/2003 | Khamene et al. |
| 2004/0034300 | A1* | 2/2004 | Verard et al. ............... 600/424 |
| 2004/0097806 | A1 | 5/2004 | Hunter et al. |
| 2004/0106869 | A1 | 6/2004 | Tepper |
| 2004/0109608 | A1 | 6/2004 | Love et al. |
| 2004/0210547 | A1 | 10/2004 | Wentland et al. |
| 2004/0249267 | A1* | 12/2004 | Gilboa ............... 600/424 |
| 2005/0085793 | A1 | 4/2005 | Glossop |
| 2005/0182295 | A1 | 8/2005 | Soper et al. |
| 2006/0184016 | A1 | 8/2006 | Glossop |
| 2006/0241577 | A1 | 10/2006 | Balbierz et al. |
| 2007/0167801 | A1 | 7/2007 | Webler et al. |
| 2007/0197896 | A1 | 8/2007 | Moll et al. |
| 2007/0232882 | A1 | 10/2007 | Glossop et al. |
| 2007/0293721 | A1* | 12/2007 | Gilboa ............... 600/117 |
| 2008/0132785 | A1 | 6/2008 | Piron et al. |
| 2008/0132911 | A1 | 6/2008 | Sobe |
| 2008/0183071 | A1 | 7/2008 | Strommer et al. |
| 2008/0242978 | A1* | 10/2008 | Simon et al. ............... 600/426 |
| 2008/0287787 | A1 | 11/2008 | Sauer et al. |
| 2009/0069679 | A1 | 3/2009 | Hibi |
| 2009/0143674 | A1 | 6/2009 | Nields |
| 2009/0221908 | A1 | 9/2009 | Glossop |
| 2009/0274357 | A1 | 11/2009 | Wilson et al. |
| 2010/0298704 | A1 | 11/2010 | Pelissier et al. |
| 2010/0298705 | A1* | 11/2010 | Pelissier et al. ............... 600/443 |
| 2010/0298712 | A1* | 11/2010 | Pelissier et al. ............... 600/459 |
| 2012/0059220 | A1* | 3/2012 | Holsing et al. ............... 600/109 |
| 2013/0211243 | A1* | 8/2013 | Zhang et al. ............... 600/424 |
| 2013/0218024 | A1* | 8/2013 | Boctor et al. ............... 600/476 |

FOREIGN PATENT DOCUMENTS

| | | |
|---|---|---|
| WO | 2004019799 A1 | 3/2004 |
| WO | 2004023103 A1 | 3/2004 |
| WO | 2007027511 A2 | 3/2007 |
| WO | 2007067323 A2 | 6/2007 |
| WO | 2009049082 A1 | 4/2009 |
| WO | 2009153723 A1 | 12/2009 |

OTHER PUBLICATIONS

Krucker, J. et al., "Electromagnetic Tracking for Thermal Ablation and Biopsy Guidance: Clinical Evaluation of Spatial Accuracy", J Vasc Interv Radiol. Sep. 2007; 18(9): 1141-1150.

Nagel, M. et al., "Electromagnetic Tracking System for Minimal Invasive Interventions Using a C-arm System with CT Option: First Clinical Results", Medical Imaging 2008: Visualization, Image-guided Procedures, and Modeling, Proc. of SPIE, vol. 6918 (2008).

Leotta, D. F. et al., "Performance of a Miniature Magnetic Position Sensor for Three-Dimensional Ultrasound Imaging", Ultrasound in Med. & Biol., vol. 23, No. 4, pp. 597-669, 1997.

* cited by examiner

LANDMARKS FOR ULTRASOUND IMAGING

REFERENCE TO RELATED APPLICATIONS

This application claims priority from U.S. Application No. 61/589,857 filed 23 Jan. 2012. For purposes of the United States, this application claims the benefit under 35 U.S.C. §119 of U.S. Application No. 61/589,857 filed 23 Jan. 2012 and entitled LANDMARKS FOR ULTRASOUND IMAGING which is hereby incorporated herein by reference for all purposes.

TECHNICAL FIELD

This invention relates to medical imaging. The invention relates specifically to methods and apparatus for guiding biopsy devices or other tools to locations within the body of a patient. The invention has particular application to ultrasound-guided biopsy planning, guiding, brachytherapy and the like.

BACKGROUND

In the diagnosis and treatment of patients, it is sometimes necessary to take small tissue samples (biopsies) from tissues within the body of a patient. For example, where the patient may have cancer or another disease of the prostate, a physician may take biopsies at a number of locations within the prostate. These biopsy samples may be analyzed in a lab to allow medical professionals to better understand the state of the patient's health and also to allow the medical professionals to plan a treatment, where necessary.

Some treatments for cancer and other tumours involve placing small radioactive seeds or other objects in the body near the locations of the tumours. Brachytherapy is one example of such treatment. In brachytherapy it is desirable to plant the seeds in locations such that, as much as possible, tumours are irradiated while normal tissues surrounding the tumours are spared.

There remains a need for easy-to-use systems and methods for assisting medical personnel to accurately introduce tools to locations within their patients. There is a particular need for such systems that provide real-time information to assist in guidance of a tool or the like that can be understood intuitively.

SUMMARY

This invention has a range of aspects. Example aspects of the invention provide ultrasound machines, systems for guided placement of medical tools for example, biopsy needles, devices for introducing brachytherapy seeds and other objects into a subject and the like, systems for facilitating guided return of a tool to a previously recorded location in a subject, systems for displaying guidance information for a surgical tool, methods for guided placement of medical tools, methods for guiding return of a tool to a previously recorded location in a subject, methods for displaying guidance information for a surgical tool, computer program products carrying machine-readable instructions for causing a data processor to control execution of a method or part thereof as described herein, and the like.

One aspect of the invention applies 2D images which include indicia to indicate 3D locations. Combinations of graphic attributes such as color, size, shape, brightness and transparency of the indicia are controlled to display information representing 3D locations in 2D images.

Another aspect of the invention applies fiducial locations to provide location tracking mechanisms that are independent of the relative positions of a patient and a tracking system base unit.

Another aspect of the invention provides systems and methods for recording in real time the locations at which interventions are performed on a patient (examples of interventions are taking biopsy samples, placing seeds or other objects in the patient, and the like).

Another aspect of the invention provides ultrasound imaging apparatus comprising: an ultrasound probe configured to transmit ultrasound signals and to receive ultrasound echo signals and an ultrasound system configured to process the ultrasound echo signals to yield a two-dimensional ultrasound image representing an image plane within a subject. A display is connected to display the ultrasound image. A position-sensing system is configured to monitor a position and orientation of the ultrasound probe in a coordinate system to yield probe position and orientation information. A processor is configured to: process the probe position and orientation information to determine: a display location in the ultrasound image corresponding to a perpendicular projection of a predetermined location onto the image plane and a distance between the predetermined location and the image plane; and superimpose on the ultrasound image on the display location marking indicia at the display location and having one or more appearance characteristics determined at least in part by the distance between the predetermined location and the image plane.

Another aspect provides apparatus for providing information regarding the relationship between the location of a selected point within the body of a patient and the location and orientation of an ultrasound probe. The apparatus comprises a processor. The processor is configured to receive first information indicating the location and orientation of the ultrasound probe and to determine, based on the first information, second information indicating the location and orientation of a 2D region within the body of the patient scanned by the ultrasound probe. The processor is configured to receive third information indicating the location of the selected point and to determine, based the second and third information fourth information indicating whether or not the selected point lies within the 2D region. The processor is configured to set location and appearance of indicia on a display based on the fourth information.

The foregoing aspects may be applied together (e.g. a single system may be configured to include all of these aspects). In the alternative, these aspects may be applied individually or in any combinations.

Further aspects of the invention and features of example embodiments are illustrated in the accompanying drawings and/or described in the following detailed descriptions.

BRIEF DESCRIPTION OF THE DRAWINGS

The appended drawings illustrate non-limiting example embodiments.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
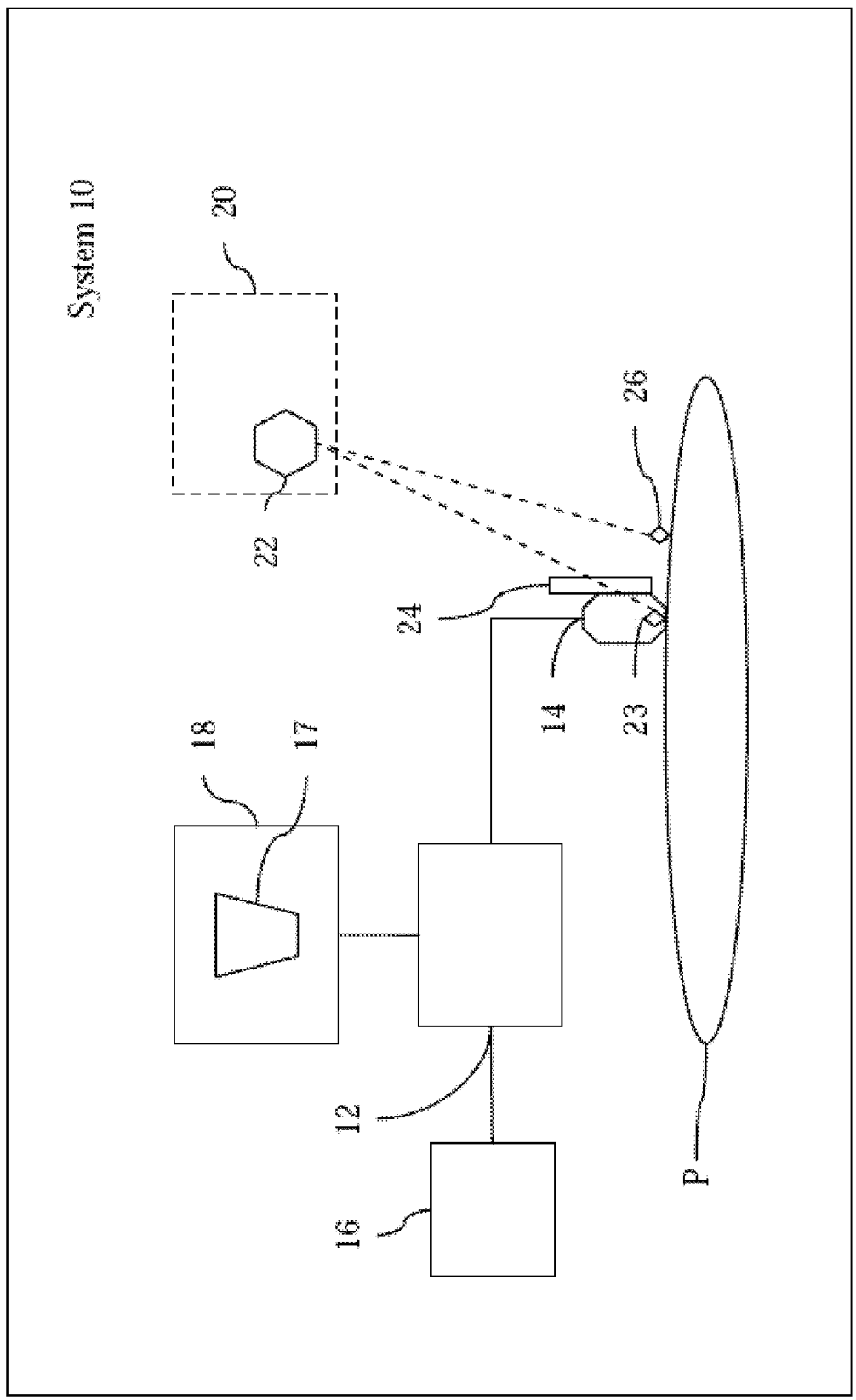
FIG. 1 illustrates schematically a system according to an example embodiment.

FIG. 1 illustrates schematically a system 10 according to an example embodiment. System 10 is being used to investigate a patient P. An ultrasound imaging system 12 has a probe 14 that sends ultrasound energy into patient P and receives echo signals from within patient P. The echo signals are processed by ultrasound system 12 to yield images 17 that are displayed on a display 18. Ultrasound system 12 may have any suitable construction. A wide range of ultrasound systems capable of generating images of structures within a patient are commercially available. Ultrasound system 12 may, for example, be or operate like such commercially-available systems.

Image 17 may be a 2D image representing a slice through a portion of patient P. For example, image 17 may comprise a B-mode image. The particular location and orientation of the plane imaged by image 17 is determined by the location and orientation of probe 14 relative to the patient P. Image 17 may be refreshed in real time such that a user can readily select a desired imaging plane by moving probe 14 and watching the resulting image 17. Ultrasound machine 12 may have a user interface 16 which allows the user to select imaging modes and/or parameters affecting the imaging modes to achieve a desired image display on display 18.

System 10 includes a 3D location system 20 which comprises a base unit 22, a sensor 23 embedded in probe 14, and an optional fiducial sensor 26. Fiducial sensor 26, when present, may be applied at a fixed location on the subject patient P. Where base unit 22 is or can be placed at a known position and orientation relative to patient P then a separate fiducial sensor 26 is not required. In such cases, base unit 22 can be considered to be the fiducial sensor 26.

System 20 may operate according to any of a wide number of principles. In some embodiments, system 20 uses magnetic fields to monitor the location and orientation of the sensor 23 in the probe 14 and the fiducial sensor 26. Various 6-degree-of freedom (6DOF) location systems are commercially available. One of these systems may, for example, be applied as 3D location system 20.

In the illustrated embodiment, system 10 incorporates a fiducial sensor 26. Fiducial sensor 26 may be removably affixed at a known location on patient P. System 20 detects the location and orientation of fiducial sensor 26 relative to base unit 22. System 20 can therefore determine the positions and orientations of other sensors relative to fiducial sensor 26. With fiducial sensor 26 affixed at a known location on patient P, base unit 22 can be freely moved around the patient P without affecting the ability of system 20 to track positions and orientations of other sensors relative to fiducial sensor 26. It is convenient but not mandatory that fiducial sensor 26 be affixed at the same spot on patient P for different study sessions.

Image 17 relates to a plane which has a known orientation relative to probe 14 and each location (e.g. each pixel) in image 17 corresponds to a known location in the image plane relative to probe 14 (the locations in the image plane that correspond to pixels in image 17 may change depending on the imaging mode).

Figure 2:
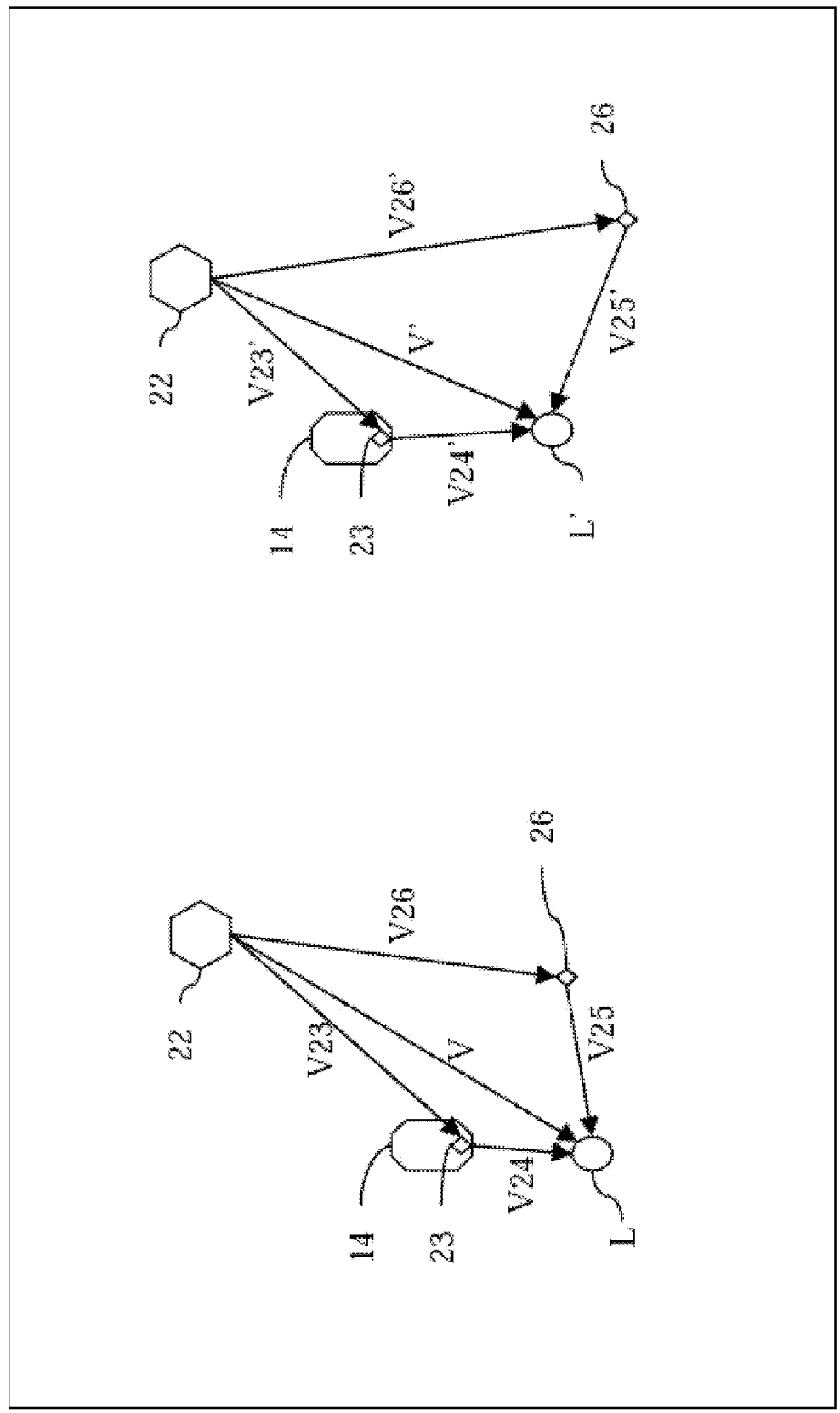
FIG. 2 is a vector diagram illustrating an example method for determining location and orientation of a probe sensor and other tracked components.

As shown in FIG. 2, system 20 may determine the location and orientation of the probe sensor 23 as vector V23 and the location and orientation of fiducial sensor 26 as vector V26 relative to base unit 22. Any location L in the present imaging plane of the probe 14 can then be derived by the ultrasound system 12 from vector V23 and the vector V24 between the point corresponding to location L and a reference location on the probe sensor 23. The sum of these vectors, shown as vector V relative to the base unit 22, may be further transformed to provide a vector V25 indicating the position of location L relative to the location of fiducial sensor 26 using the known vector V26. Vector V25 indicates the position of location L relative to fiducial sensor 26.

Information identifying one or more locations, such as location L, may be stored for future reference. Such information may, for example, be applied to guide a tool to the location in future and/or to obtain an ultrasound image in the same plane relative to patient P as a current ultrasound image. The information stored may comprise, for example, vector V25 corresponding to one or more locations L. The stored information may also comprise stored fiducial data (e.g. vector V26). In some embodiments, locations are initially stored in memory and then saved to files in a data store for subsequent reloading.

System 20 may track the position of a location L relative to the imaging plane of probe 23. In general, probe 23 and its imaging plane may be moving relative to base unit 22. The relative locations of base unit 22 and fiducial sensor 26 may also be changing. System 20 may be configured to update a vector V25' indicating the position of a location L relative to fiducial sensor 26 (located at a current position V26') by applying spatial transformations (which may comprise rotations and/or translations) to vector V25. Vector V25' may be converted back to a vector V' indicating the current position of location L relative to base unit 22, and then this current position of location L may be projected perpendicularly to the current imaging plane as L'.

The system may display an indicia at a location in the image corresponding to L'. The indicia identifies the location L' in the image which indicates the perpendicular projection of location L into the current image plane. Depending on the relative distance of location L to the imaging plane, the indicia may be displayed with different colors, sizes, shapes and/or brightness.

For instance in some embodiments, when the image plane is positioned and oriented such that location L falls in the imaging plane, the indicia may comprise a large green icon or other marker. While location L is out of the image plane in the near field (i.e. on a front side of the image plane), the color of the marker may be gradually mixed with blue with the amount of blue determined by the distance of location L from the image plane. The marker may be displayed as being pure blue at a threshold distance. In some embodiments the threshold distance is a maximum viewing depth. While location L is out of the image plane in the far field (i.e. on a rear side of the image plane), the color of the marker may be mixed with red. The amount of red may be determined by the distance of location L from the image plane. The marker may be displayed in a pure red color when location L is at a threshold distance out of the image plane.

Colors other than green, blue and red may be used in alternative example embodiments. For example, some embodiments are similar to the embodiment described above except that green, blue and red are respectively replaced with a first color, a second color and a third color (where the first, second and third colors are any three distinguishable colors). Characteristics other than color and size may be varied instead of or in addition to color and/or size. Other characteristics that may be varied include, for example, brightness, line thickness (width), line pattern, and the like.

Figure 3:
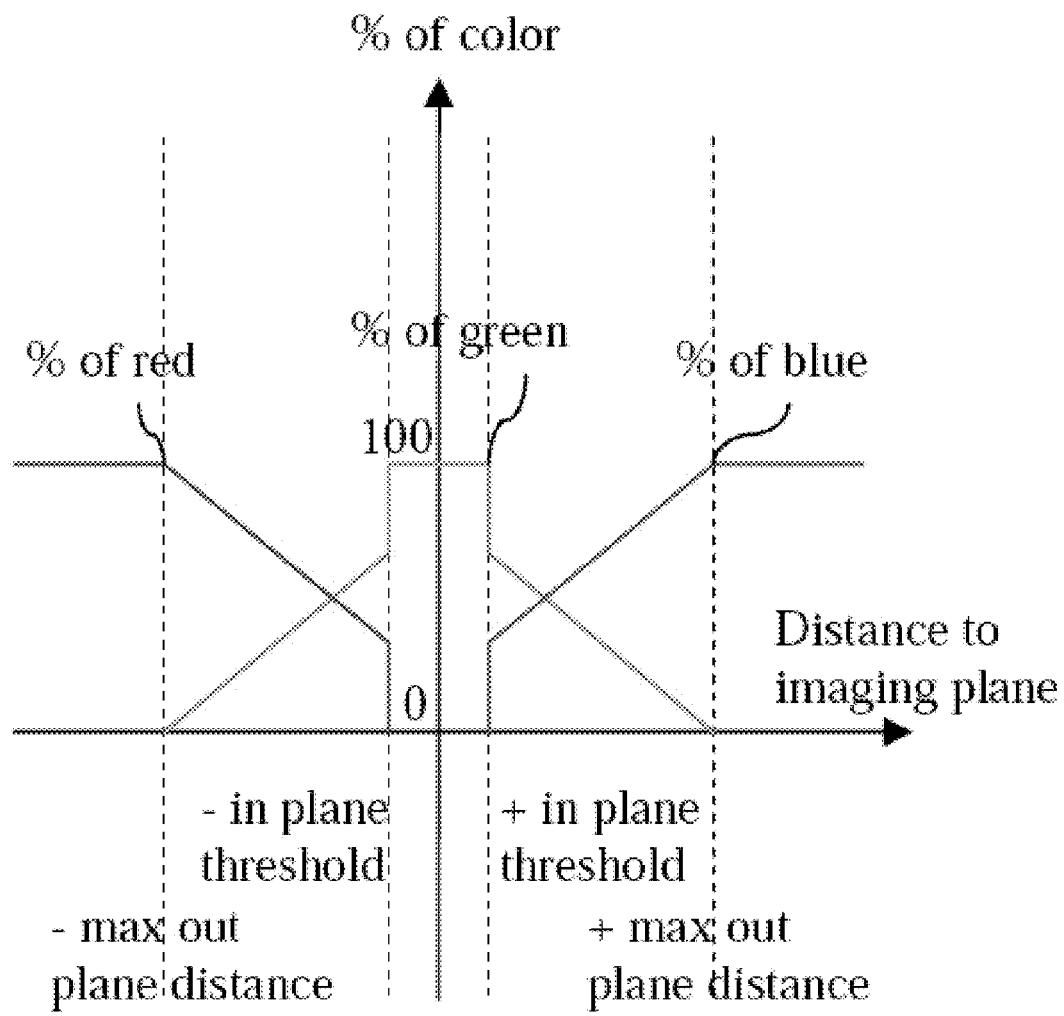
FIGS. 3 and 4 are charts that illustrate example ways in which the color and/or size of a marker indicating a location in an image may be controlled to indicate the distance between the location and the image plane and the current side of the image plane on which the location is currently sited.
Figure 4:
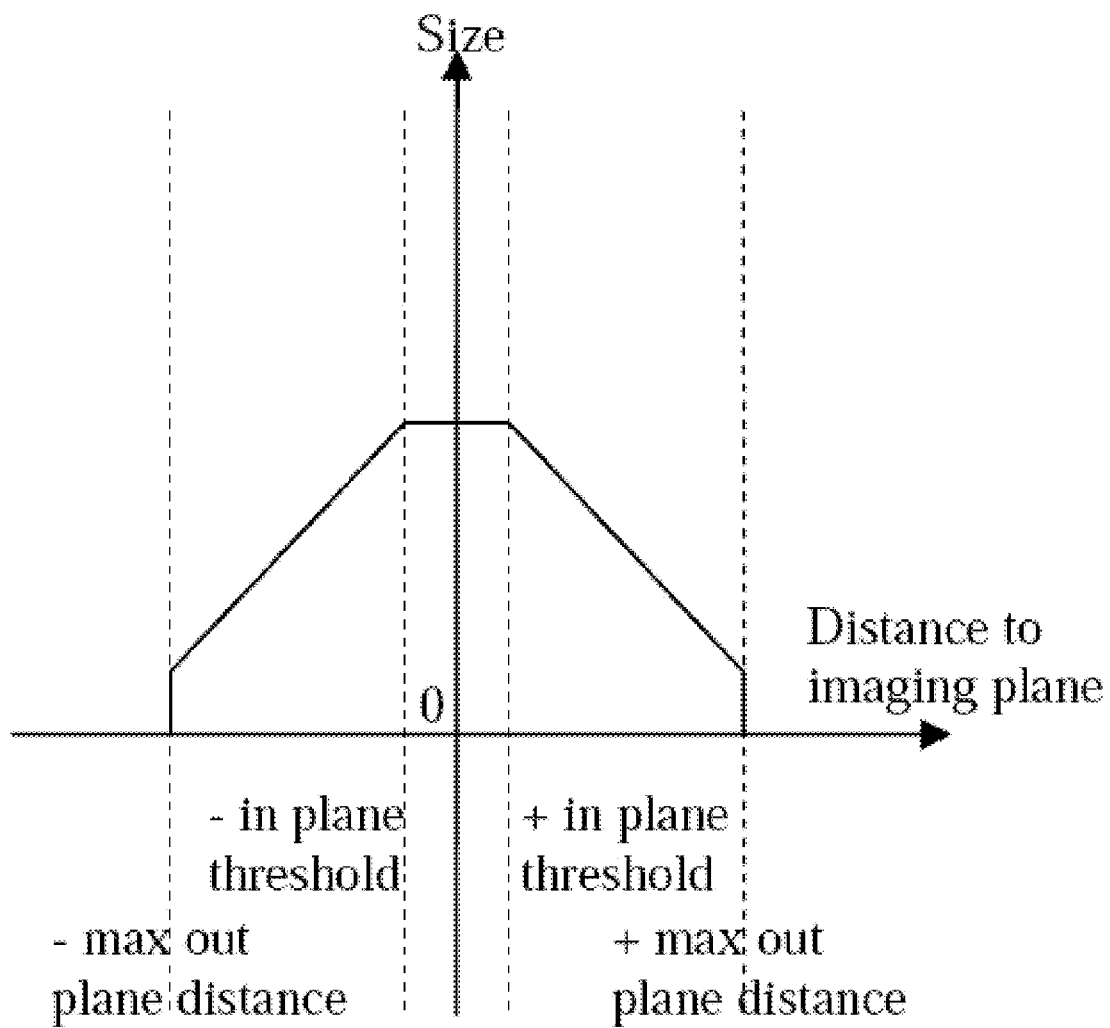

The size of the marker may also be varied based on the distance of location L from the image plane. For example, the marker may be made smaller with increasing distance from the image plane on either side of the image plane. FIGS. 3 and 4 are charts that illustrate example ways in which the color and/or size of a marker indicating location L may be controlled to indicate the distance between location L and the image plane and the side of the image plane on which location L is currently.

The markers may, for example, comprise shapes. The shapes are un-filled in some embodiments. In some embodiments the shapes are simple geometric shapes such as circles, squares or triangles.

System 10 may provide the ability to record the precise locations at which biopsy samples are taken. For example, the triggering of a biopsy device (e.g. tool 24) to remove a biopsy sample from patient P may automatically generate a signal that causes one or more positions indicative of the location from which the biopsy sample was extracted (as determined by position monitoring system 20) to be preserved in a memory. In the alternative, a separate control such as a foot pedal or button may be provided to allow the physician to signal when the surgical tool 24 is in the location at which the surgeon intends to operate or has operated the tool 24 to extract a biopsy sample.

The location at which a biopsy sample is taken may be determined by directly measuring the position (for example by tracking the position of a surgical tool used to acquire the biopsy sample with system 20 or by using a surgical tool with a guide which places the surgical tool at a known location relative to a sensor being tracked by position sensing system 20. In the illustrated embodiment, system 10 comprises a surgical tool 24, which might be a biopsy guide, or a tracking sensor enabled needle. A biopsy guide may be mounted to probe 14 such that there is a known relationship between the probe 14 (hence sensor 23) and the location where a biopsy sample will be withdrawn into the tool. The biopsy guide may be arranged such that the location at which the biopsy sample is taken is in an imaging plane of the images acquired by probe 14. From the known relationship between the biopsy location and probe 14 (as determined by the biopsy guide) the location of the actual biopsy site relative to the fiducial sensor 26 can be calculated and recorded.

In the case where a tool used to acquire a biopsy sample comprises a needle with a tracking sensor which is monitored by position sensing system 20, the location of the actual biopsy site relative to the tracking sensor of the needle is known from the construction of the needle. The location of the actual biopsy site relative to fiducial sensor 26 can be determined in a manner similar to that illustrated in FIG. 2.

Figure 5A:
FIGS. 5A, 5B and 5C illustrate marking locations in an image based on position of a guided tool, position of a tracked free-hand tool and by direct marking on the image.
Figure 5B:
Figure 5C:

Embodiments may be provided which permit locations of biopsy samples or other operations to be recorded in one or more of several different ways. Such embodiments may be used to record exactly where biopsy samples have been taken. For example, where samples are taken with a tool guided by a biopsy guide, a physician may cause apparatus to record a biopsy location with one single push on a button or a footpad. Such a control input may record a location of the biopsy sample and cause display of a marker at a location where the guide causes the biopsy sample to be taken, as shown for example in FIG. 5A. Where the biopsy sample is acquired by a needle or other biopsy devices equipped with tracking sensor, the control input (e.g. push of a button or pedal) will record a location of the tip of the needle and mark that location as illustrated for example in FIG. 5B. If none of the above devices is used the physician may use a user interface to manually mark a biopsy location in the current image plane. 3D coordinates of this location may be stored. Markers indicating the location may be shown as illustrated for example in FIG. 5C.

The information provided by 3D location system 20 and ultrasound system 12 allows determination of the location and orientation of points in the image plane and biopsy sites from various surgical tools 24 all relative to the fiducial sensor 26.

The positions of recorded locations relative to the fiducial sensor 26 can then be projected perpendicularly back on the active imaging plane as the relative relationship of the sensor 26 and probe sensor 23 is tracked by the system 20. Thus the system 10 permits the 3-dimensional locations within patient P to be represented in the 2D image 17 intuitively with different colors, sizes, shapes and/or brightness etc.

In some embodiments, system 10 comprises a programmed data processor that receives position data from 3D location system 20 and determines the 3-dimensional location within patient P of pixels of image 17 as well as the location of surgical tool 24 relative to the current image plane. The data processor may be a separate stand-alone data processor or may be integrated with 3D location sensing system 20 or ultrasound system 12 or some other component of system 10, for example.

A physician may remove a number of biopsy samples from a particular organ. For example, a typical prostate biopsy may involve the taking of several biopsy samples. In some cases, a biopsy of the prostate may involve taking from a few biopsy samples to about 25 or so biopsy samples. The samples may each be taken at a different location within the prostate (or other organ being studied). System 20 may be operated to obtain information relevant to the locations at which each of these biopsy samples was acquired. System 10 may record this information to permit: the biopsy sites to be identified in future imaging; future biopsies to be taken at or near the same locations where the biopsies were taken; brachytherapy seeds or other objects to be inserted at the location at which a biopsy sample was acquired, etc.

Figure 6:
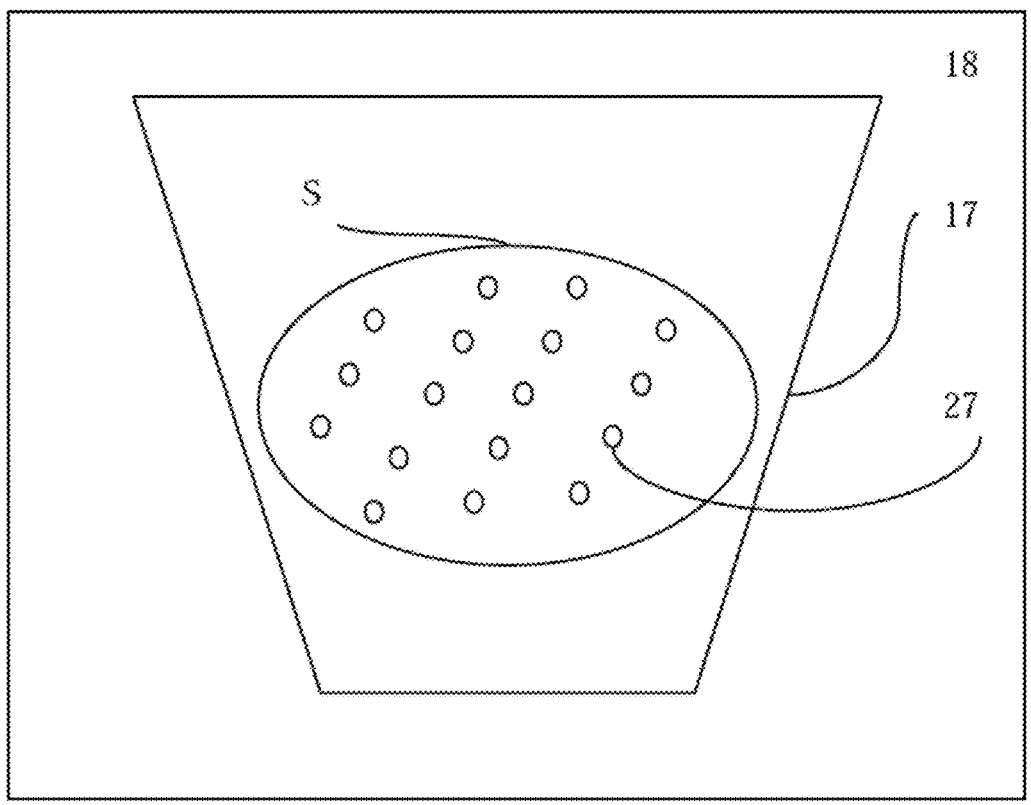
FIG. 6 schematically shows an example image which includes a portion of an organ and marked locations for acquiring biopsy samples.

In some embodiments, a system 10 may assist in planning an array of locations from which biopsy samples may be taken. For example, the system may calculate locations in three dimensions of an array of points for taking biopsy samples. In some embodiments, the array of locations may be determined relative to an initial location of tool 24. For example, a physician may insert tool 24 to a location at which it is desired to take a first biopsy sample. System 10 may then compute an array of points which are spaced apart from that initial location. In some embodiments, system 10 detects the boundaries of an organ within which the biopsy samples are to be taken (for example, by detecting edges of the organ in image data) and determines locations for taking biopsy samples that are evenly spread out throughout the organ or spread throughout the organ in a predetermined manner. User input may be provided to indicate the number and or density of the biopsy samples. FIG. 6, for example, shows an image which includes a portion of an organ S. System 10 has computed locations 27 corresponding to suggested locations for acquiring biopsy samples and has added markers indicating those locations to image 17.

It can be desirable to provide a mechanism to guide a user back to the locations at which biopsy samples were taken at a later time. The recorded locations at which the biopsy samples were taken may be used subsequently to guide a user to return to the location(s) at which any or all of the biopsy samples were taken. One example of a situation in which this may be desirable applies to the case where laboratory investigations of one or more biopsy samples find that tissue is abnormal. It may be decided to implant a brachytherapy seed or implanted drug-dispenser at the location of the particular biopsy sample. System 10 may be used to guide the user back to the same location from which the biopsy sample was taken. In this case, the user may be using a tool which permits implantation of a brachytherapy seed or other object at that location. As another example, it may be desirable to repeat a biopsy at a subsequent time to recheck results of an earlier biopsy.

System 10 may incorporate novel systems and methods for one or both of indicating the relationship between the current location and orientation of the imaging plane and one or more predefined locations within a patient; and indicating the relationship of the current location and orientation of a surgical tool, such as a biopsy probe to such predefined locations. A user may use these systems and methods in order to one or both: move probe 14 such that the imaging plane passes through a previously determined location in the patient; and insert a surgical tool 24 to interact with that previously determined location. It may be desired, for example, to take another biopsy sample at the previously determined location, implant a brachytherapy seed or other apparatus at that location, withdraw fluids from the location, or inject a drug or other material at the location, or the like.

Some embodiments have the particular advantages that they provide highly intuitive feedback to a user and also can be implemented with relatively simple graphics. In some embodiments, indications of the relative location of a surgical tool and or a predetermined location relative to the current image plane are given by superimposing graphic elements on image 17. The graphic elements may be shown at a location on image 17 which coincides with the projection of the location of the surgical tool or predetermined location into the current image plane. The projection may be a perpendicular projection for example.

The colour, size, and/or shape of the graphic element may be controlled based upon the perpendicular distance from the surgical tool or predetermined location to the image plane. In some embodiments as shown in FIG. 3, the colour of the graphic element changes with the signed distance between the relevant location and the image plane. For example, when the location of the surgical tool or the predetermined location is in (coincides with) the image plane to within some tolerance the colour of the graphical element may be green. When the location is displaced out of the image plane in one direction, the colour of the graphical element may be displayed as blue. When the location is displaced out of the image plane and on the other side of the image plane the colour of the graphical element may be red.

In some embodiments, the hue of the graphical element may change as the location moves relative to the image plane (such movement may be caused, for example, by moving ultrasound imaging probe 14) thereby changing the relative locations of the imaging plane a predetermined location within patient P and/or by moving the relative locations and/or orientations of surgical tool 24 and probe 14. The hue may change essentially continuously or in steps.

In some embodiments, the brightness and/or transparency of the graphical element are altered in response to the distance between the location and the current imaging plane. For example, the brightness and/or transparency of the graphical element may be controlled such that the graphical element is most visible when in the imaging plane. The brightness and/or transparency of the graphical element may be controlled such that as the location is displaced out of the imaging plane the visibility of the graphical element gradually diminishes with increasing separation between the location and the imaging plane. In some embodiments, when the location is far enough away from the imaging plane the graphical element is not visible at all or is barely visible.

In some embodiments, the size of the graphical element varies with the distance between the imaging plane and the location. For example, the graphical element may have a certain size when the location is in the imaging plane. As the relative position of the location and the imaging plane changes such that the location is farther from the imaging plane, the graphical element may be larger for displacements of the location to a first side of the imaging plane and may be smaller for displacements of the location to a second side of the imaging plane opposed to the first side. In other embodiments the size of the graphical element may be made smaller as the distance from the imaging plane increases (in both the near-field and far-field sides of the imaging plane) as shown in FIG. 4.

The shape or other feature of appearance of the graphical elements may indicate the natures of the location. For example, a graphical element indicating a current location of a surgical tool may have one shape or other appearance feature whereas a graphical element indicating the location relative to the current imaging plane of a predetermined location within the patient may have a different shape or appearance feature. Particularly, to differentiate the current set of markers from the recorded history markers for the identical locations, a different shape or other appearance feature may be superimposed on the current imaging plane.

Figure 7A:
FIGS. 7A, B, and C show example images overlaid with indicia indicating the locations of a number of points relative to an imaging plane.

FIGS. 7A, B, and C illustrate some specific example embodiments. FIG. 7A shows an image with superposed indicia (depicted as circles) indicating the positions of various locations relative to an imaging plane in which the image is taken. The geometry of the locations is indicated schematically in FIG. 7D which shows imaging plane 28 and locations in and out of imaging plane 28. A location 2 (which may be the location of a predetermined location within a patient P or a location of a surgical tool 24) is in imaging plane 28 and is located relative to transducer 14 a distance R at an angle θ. Another location 3 is spaced apart from imaging plane 28 on one side (in the illustrated embodiment in front of imaging plane 28) by a distance D1. Another location 4 is in front of and spaced apart from imaging plane 28 by a second distance D2. A location 1 is spaced behind image plane 28 by a distance D1. Another location 0 is spaced behind image plane 28 by a distance D2. In this example embodiment, all of locations 2, 3, 4, 1, and 0 are on a line intersecting with imaging plane at location 2.

Figure 7B:
FIG. 7D illustrates the geometry of FIG. 7A.
Figure 7C:
Figure 7D:
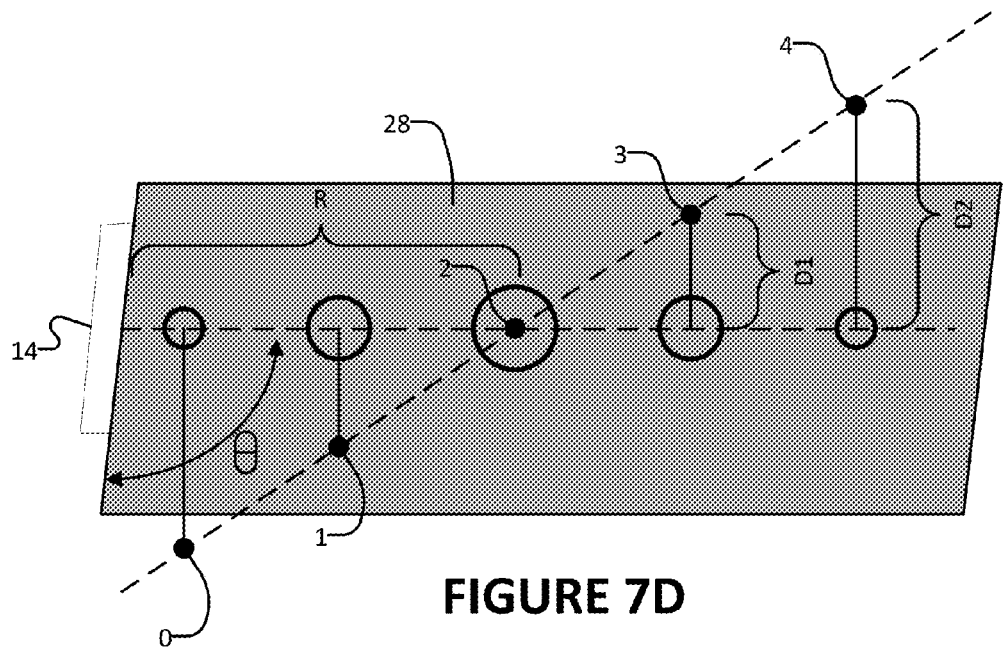

FIG. 7B illustrates an image 17 of imaging plane 28 with the same points but at a greater angle with the imaging plane. And FIG. 7C shows all the points forming a line perpendicular to the imaging plane. Circle 2 may be shown in the colour green to indicate that location 2 is in imaging plane 28. For locations displaced along the line toward the front of plane 28 both the size and color of graphical elements indicating those locations may be different from those of circle 2. For example, as indicated in FIG. 7B, the graphical element to indicate location 3 may be a circle 3 that is decreased in size relative to circle 2 and may also be displayed in a different colour. This immediately indicates to a user that a location in question is out of the imaging plane and, from the size of the circle, the user can get an indication of how far out of the imaging plane the location is located.

This information and the size of the graphical element may be adjusted in real time such that the user can get immediate graphical feedback which enables the user to position imaging plane 28 such that the location in question lies within imaging plane 28. Real-time changes in the size of the circle (or other graphical element) as probe 14 and or tool 24 are moved provide intuitive feedback that helps a user to make the image plane coincide with the targeted location. If desired, a user can also use the real-time feedback provided by the overlay of graphical elements on image 17 to place the targeted location at a desired position in the image 17.

As indicated in FIG. 7B, if the location in question is displaced to the other side of image plane 28, for example at one of locations 3 or 4, graphical element may be indicated by a circle 3 and 4 which is smaller than circle 2 and may also be of a different colour.

It has been found that the use of simple circular graphical elements which is controlled so that its size and color change as described above superposed on a 2D ultrasound image provides a surprisingly intuitive and easy-to-use system for accurately guiding an image plane to image a target location and also for guiding a tool to the target location.

Consider the following use case. A physician has previously acquired a set of biopsy samples from within the organ of a patient. The physician marked the locations at which the biopsy samples were taken using system 10 such that system 10 has stored coordinates directly or indirectly indicating the three dimensional locations at which those samples were acquired from the patient. The three dimensional locations may be known relative to any suitable fiducial point on the patient. The fiducial point may be indicated by a fiducial sensor (e.g. sensor 26 of FIG. 1), a brace or other device that holds the patient in a specific location relative to base unit 22 in a repeatable manner, a fiducial location that can be observed either manually or automatically marked in an image, as shown in FIG. 7A/7B/7C as triangle markers for instance, or the like).

The physician first manipulates ultrasound transducer 14 until imaging plane 28 coincides with one or more of the previous biopsy locations. The physician can do this by observing the graphical indicators in image 17. The changing sizes and colours of the graphical indicators give the physician direct visual feedback which help the physician to position transducer 14 such that the one or more locations at which biopsy samples were previously taken are in imaging plane 28 of the transducer. Next, while the physician holds transducer 14 in this location and orientation, the physician prepares to insert a surgical tool 24 so as to enter the patient and reach the marked location. For example, the physician may wish to implant a brachytherapy seed at the point at which a biopsy sample was previously taken or another biopsy sample in the same location at which the previous biopsy sample was taken. System 10 records the location and orientation of the surgical tool. From the orientation of the surgical tool, the system can determine a point at which the surgical tool will intersect the image plane if inserted to the patient along its current trajectory. This location may be displayed by means of a graphic indicia on image 17. The physician may move the surgical tool and/or adjust its orientation until the indicia showing where the surgical tool will intersect the imaging plane coincides with the graphic indicia indicating the prior biopsy location on the imaging plane.

The physician now has confidence that he or she can insert the surgical tool into the patient to intersect the imaging plane exactly at the desired location. Indicia on the display may be provided to indicate the progress of the surgical tool toward the imaging plane. This indicia may also change size and/or colour to indicate the progress of the surgical tool toward the imaging plane and to indicate the coincidence of a specific location on the surgical tool (for example, a tip at which a brachytherapy seed is dispensed or an opening into which a biopsy sample is drawn). The physician may observe this indicia, while holding the transducer so as to keep the desired location in the imaging plane. When the indicia indicates that the surgical tool is at the correct position, the physician may operate the surgical tool to dispense and/or withdraw something at the location or to otherwise interact with the location.

In some cases, the locations of organs may change relative to fiducial points on a patient. This may occur, for example, if a patient loses weight, gains weight, or the like in between the time that a location is first stored and a subsequent time at which it is desired to return to the location with a surgical tool or the like. In some embodiments, a form of organ registration is provided. In such embodiments, the locations of points within an organ are recorded with information that allows determination of the relative locations of those points to key points on the organ itself. For example, the locations of the points may be recorded together with locations of recognizable points on an organ (e.g. the left-most and right-most points on the organ in a sagittal view, the extremities of the organ in a coronal view, the location of a specific recognizable feature on an organ, for example, the point at which a particular duct, blood vessel, or the like enters or leaves the organ). By locating and marking these fiducial points of the organ in images produced in a subsequent imaging session, the original points may be located relative to the fiducial points of the organ itself. This may provide a more accurate way to return to those original locations, even if the organ itself has moved somewhat relative to the skeletal structure of the patient in an intervening period.

In some embodiments, system 10 has a user interface which allows a user to adjust the thickness of a slab on either side of the imaging plane within which graphical indicators for locations within that slab are displayed. By reducing the thickness of the slab, the displayed image can be simplified to show fewer locations, increasing the thickness can allow the user to see a wider range of locations in the vicinity of the imaging plane and thus allows the user to rapidly find a location of interest to focus on.

In some embodiments a system allows a user to control by way of a user interface what locations will be indicated on the display. For example, the system may have records of a large number of locations in a patient. The locations may be in different categories. For example, locations at which biopsy samples were taken, locations at which, seeds or drugs were placed, locations of fiducial features of the patient, etc. Each of these categories may have one or more sets of locations.

The system user may permit the user to select what locations are to be indicated on the display by category, set and/or individual location.

In the above illustration, surgical tool 24 was shown to be a free-hand surgical tool. In some embodiments, a guide may be fixed to ultrasound probe 14. The guide may be adjusted to define a trajectory for a surgical tool or the guide may be fixed. Where the guide is fixed, it is optional but not necessary for the surgical tool to include a position sensor detectable by the position monitoring system 20. In such embodiments, the location at which a surgical tool inserted through the fixed guide will intersect the imaging plane will be known from the geometry of the guide. The known location may automatically be located by an indicia in the image. A user may move the ultrasound probe (together with the attached guide) until the indicia coincides with the desired location in the imaging plane.

Figure 8:
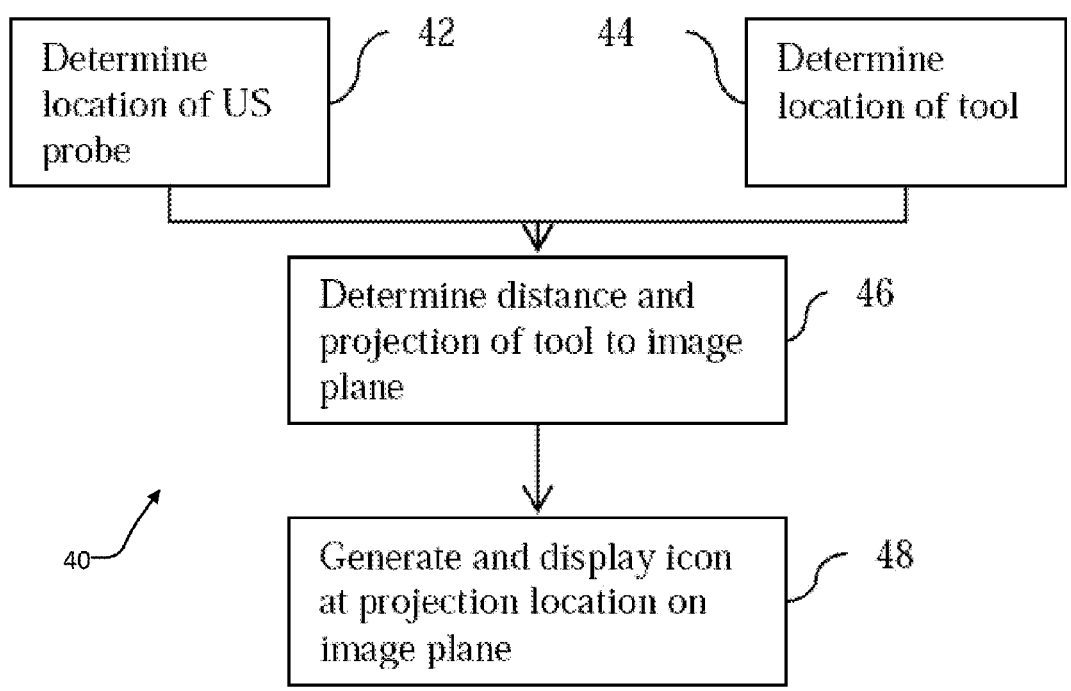
FIG. 8 is a flowchart illustrating one method of use of a system according to an embodiment of the invention.

FIG. 8 is a flowchart illustrating one method of use of a system according to an embodiment of the invention. In method 40, block 42 determines the location of an ultrasound probe. Block 44 determines the location of a surgical tool. From these two locations, the system can determine the distance of the tool from the imaging plane and the projection of the trajectory of the tool into the image plane. This is done in block 46.

Block 48 generates an icon and displays it on the image 17. The appearance of the icon is variable depending on the distance of the tool from the imaging plane. For example, the colour and/or size and/or transparency, and/or brightness, and/or hue of the icon may be set based upon the distance determined in block 48. In some embodiments the icon is a circle. In block 48, the icon is displayed on a two dimensional image of the area in an imaging plane based upon the location of the intersection determined in block 46.

Figure 9:
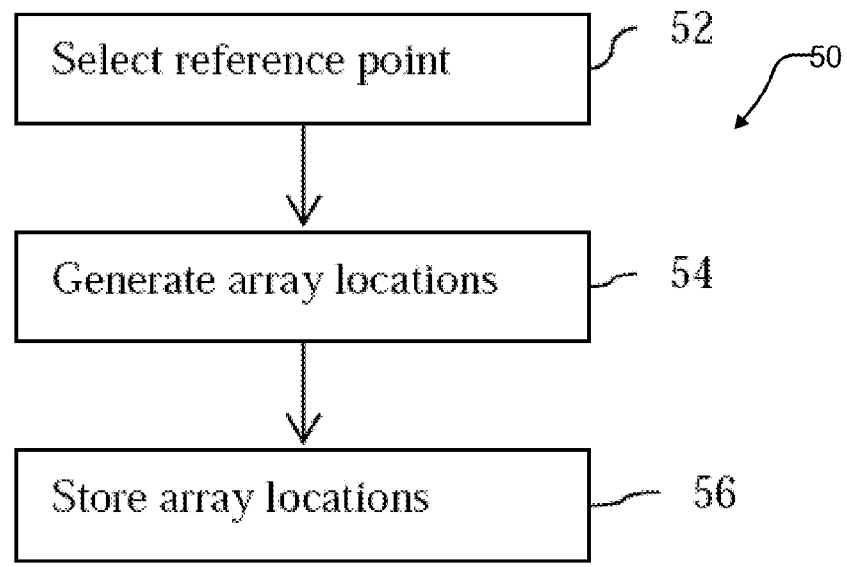
FIG. 9 is a flowchart illustrating a method according to another embodiment.

FIG. 9 shows a method 50 according to another example embodiment of the invention. Method 50 is useful for generating a set of array locations, for example locations at which biopsy samples may be taken. In block 52 a reference point is selected. Block 52 may, for example, comprise indicating on an image the location of a characteristic feature of an organ or a fiducial location within a person's body or the like. Block 52 may also comprise inserting a surgical tool, such as a biopsy needle, to a location at which a first biopsy will be taken. Block 54 generates an array of additional locations which are located relative to the first location. Block 56 stores the array of locations, including the first location. Once these locations are stored, then navigation as described above may be performed in order to guide a user to any of the locations in the stored array. An example application of method 50 applies where it may be desired to acquire biopsy samples at locations surrounding a location of a previously-acquired biopsy sample. For example, the previous sample may have been tested and may be suspicious. It may be desired to acquire additional biopsy samples at locations surrounding (in 3D) the previous sample.

Figure 10:
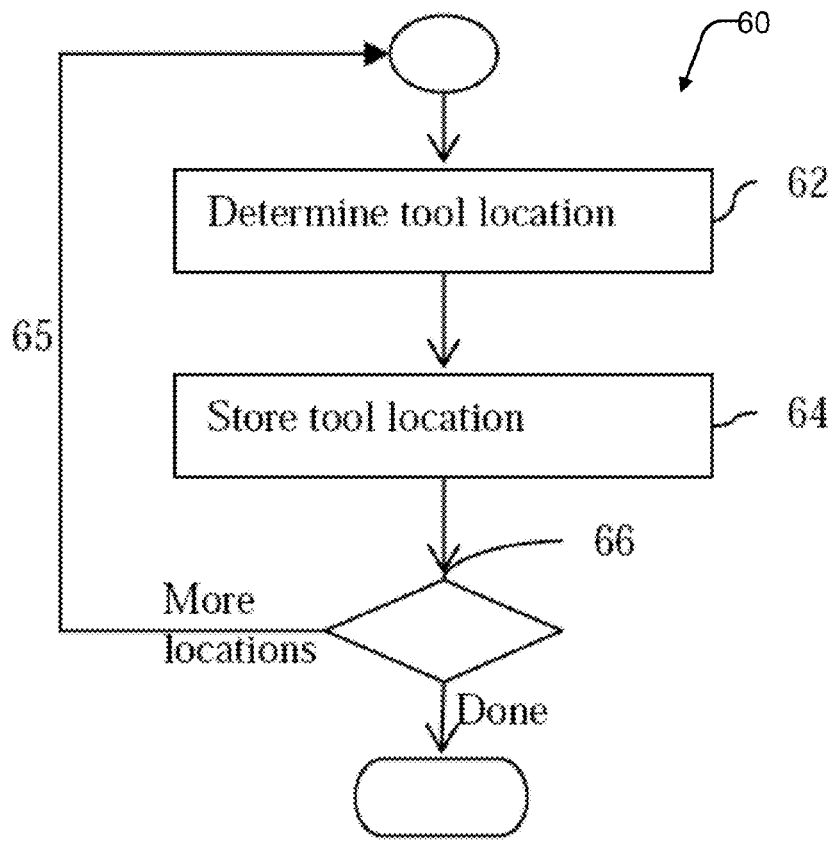
FIG. 10 is a flowchart illustrating a method according to another embodiment.
Figure 11:
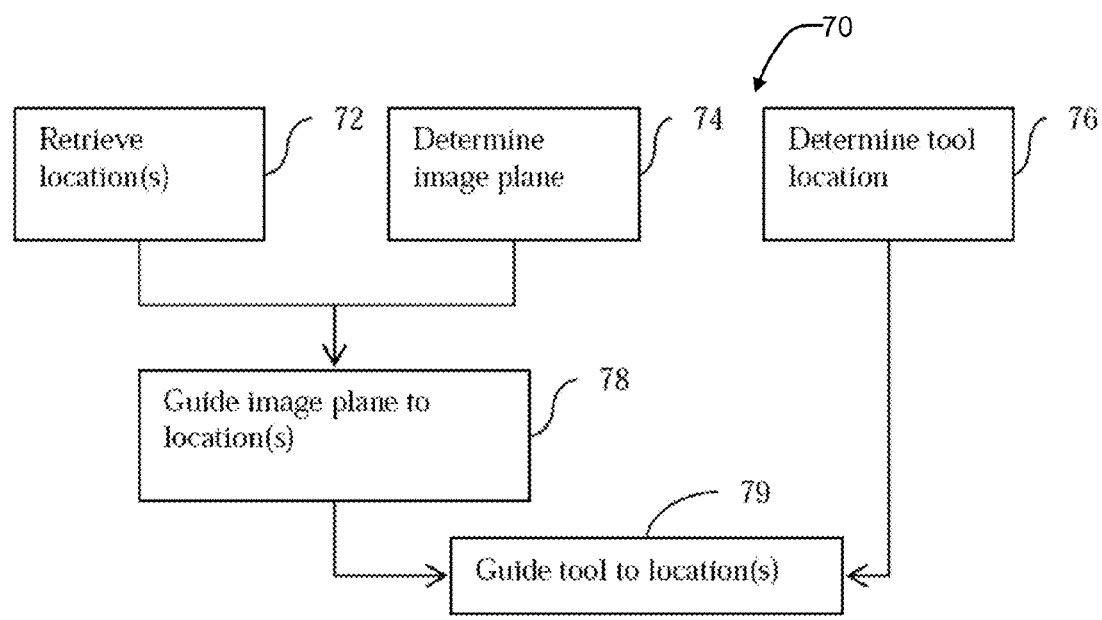
FIG. 11 is a flowchart illustrating a method according to another embodiment.

FIG. 10 illustrates a method 60 according to another example embodiment for storing locations. Method 60 begins at block 62 by determining a location of a tool. For example, block 62 may determine the current location and orientation of a biopsy tool. In block 64, the location is stored. Loop 65 is repeated for any desired number of distinct locations. Block 66 determines whether more locations are to be determined. If so, loop 65 is repeated. Otherwise, method 60 ends. FIG. 11 shows another example embodiment of the invention. Method 70 includes block 72, 74, and 76. Block 72 retrieves previously stored locations. Block 74 determines a current location of an image plane and block 76 determines a current location of a tool, such as a biopsy needle, or the like. In block 78, a user is assisted to guiding an image plane of the imaging device so that one or more of the retrieved locations coincides with the image plane. This may be done through the use of graphic indicia as described above, for example. Once the location or locations are coincident with the image plane then block 79 is performed. In block 79, indicia are displayed to assist a user in guiding the surgical tool to the desired locations. This may be done with the assistance of indicia as described above.

Embodiments of the invention may be implemented using specifically designed hardware, configurable hardware, programmable data processors configured by the provision of software (which may optionally comprise 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks in example embodiments are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences.

The invention may also be embodied in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software combined with a processor to execute the software. For greater clarity, "software" includes any instructions executed on a processor, and may include (but is not limited to) firmware, resident software, microcode, and the like.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

While a number of exemplary aspects and embodiments have been discussed above, those of skill in the art will recognize certain modifications, permutations, additions and sub-combinations thereof.

What is claimed is:

1. An ultrasound imaging apparatus, comprising:
   an ultrasound probe configured to transmit ultrasound signals and to receive ultrasound echo signals;
   an ultrasound system configured to process the ultrasound echo signals to yield a two-dimensional ultrasound image representing an image plane within a subject;
   a display connected to the ultrasound system and the display displays the ultrasound image;
   a position-sensing system configured to monitor a position and orientation of the ultrasound probe in a coordinate system to yield probe position and orientation information;
   a processor configured to:
      process the probe position and orientation information to determine: a display location in the ultrasound image corresponding to a perpendicular projection of a predetermined location onto the image plane and a distance between the predetermined location and the image plane within a slab of a thickness defined by a positive slab surface and a negative slab surface which are a positive and negative distance from the image plane respectively; and
      superimpose on the ultrasound image a display location marking indicia at the display location, and the indicia having one or more appearance characteristics determined at least in part by the distance between the predetermined location and the image plane within the slab, and the one or more appearance characteristics include a hue which is a continuous function of three colors within the slab.

2. The apparatus according to claim 1, wherein the position sensing system comprises a fiducial sensor configured to be removeably applied to the subject at a predetermined fixed location relative to the subject, the position sensing system is configured to monitor a position and orientation of the fiducial sensor and to determine position and orientation of the predetermined location relative to the fiducial sensor and the processor is configured to use the fiducial sensor position and orientation in determining the display location and the distance between the predetermined location and the image plane.

3. The apparatus according to claim 2, further comprising a tool configured to be inserted into the subject,
   wherein the position-sensing system is configured to monitor a position and orientation of the tool to yield tool position and orientation information and the processor is configured to process the tool position and orientation information to determine a position of a point on the tool relative to the image plane, and determine a relative location of the point to at least one recognizable point of an organ in the subject.

4. The apparatus according to claim 3, wherein the processor is configured to process the tool position and orientation information to determine a tool location in the ultrasound image corresponding to a perpendicular projection of the point on the tool onto the image plane and a distance between the point on the tool and the image plane, and to superimpose on the ultrasound image on the display, tool indicia located at the tool location having one or more appearance characteristics determined at least in part by the distance between the point on the tool and the image plane.

5. The apparatus according to claim 4, wherein the tool indicia and the location marking indicia are different in appearance.

6. The apparatus according to claim 3, wherein the processor is configured to determine from the orientation of the tool an intersection point at which the tool will intersect the image plane if inserted to the subject along a current trajectory and to superimpose on the ultrasound image, indicia indicating a location in the ultrasound image corresponding to the intersection point.

7. The apparatus according to claim 3, wherein the processor is configured to store information specifying the position of the point on the tool in response to a triggering event.

8. The apparatus according to claim 7, comprising a user interface wherein the triggering event comprises actuation of a control of the user interface.

9. The apparatus according to claim 7, wherein the tool comprises a biopsy device and the triggering event comprises operation of the biopsy device to acquire a biopsy sample.

10. The apparatus according to claim 1, wherein the processor is configured to suppress display of the location marking indicia when the distance between the predetermined location and the image plane exceeds the positive and negative surfaces defined by the slab.

11. The apparatus according to claim 10, wherein the distance of the positive and negative surfaces defined by the slab is adjustable by way of a user interface control.

12. The apparatus according to claim 1, wherein the continuous function of three colors includes:
   a first color contribution which decreases linearly from a maximum to zero according to a distance between the positive slab surface and the image plane, and is zero between the image plane and the negative slab surface;

a second color contribution which increases linearly from zero to a maximum according to a distance from the positive surface or the negative surface to the image plane; and a third color contribution which decreases linearly from a maximum to zero according to a distance between the negative slab surface and the image plan, and is zero between the image plane and the positive slab surface.

13. The apparatus according to claim 12 wherein the location marking indicia comprises an outline shape and a size of the outline shape is set based upon the distance between the predetermined location and the image plane.

14. The apparatus according to claim 1, wherein the one or more appearance characteristics comprise one or more of: color, brightness, transparency, size, or shape.

15. The apparatus according to claim 1, wherein the processor is configured to:

process the probe position and orientation information to determine for each of one or more additional predetermined locations: an additional display location in the ultrasound image corresponding to a perpendicular projection of the additional predetermined location onto the image plane and a distance between the additional predetermined location and the image plane, and the one or more additional predetermined locations are selected from one or more previously recorded locations; and superimpose on the ultrasound image at the additional display location an additional location marking indicia having one or more appearance characteristics determined at least in part by the distance between the additional predetermined location and the image plane.

16. The apparatus according to claim 1, wherein the processor is configured to generate an array of additional locations which are located relative to the predetermined location and to store the locations of the array of additional locations as additional predetermined locations.

17. The apparatus according to claim 1, wherein the processor is configured to update the position and appearance of the location marking indicia in real time.

18. An apparatus for providing information regarding a relationship between a location of a selected point within a body of a patient and a location and orientation of an ultrasound probe, the apparatus comprising a processor,
wherein:
the processor is configured to receive first information indicating the location and orientation of the ultrasound probe;
the processor is configured to determine, based on the first information, second information indicating the location and orientation of a 2D region within the body of the patient scanned by the ultrasound probe;
the processor is configured to receive third information indicating the location of the selected point selected from a plurality of recorded points;
the processor is configured to determine, based the second and third information, fourth information indicating whether or not the selected point lies within the 2D region;
the processor is configured to set location and appearance of indicia on a display based on the fourth information, wherein the appearance of the indicia includes a hue which is a continuous function of three colors;
the processor is configured to determine, based on the second information and the third information, fifth information indicating a distance between the selected point and a point within the 2D region which is closest to the selected point; and
the processor is configured to control an appearance of the indicia based at least in part on the fifth information, wherein the continuous function of three colors is defined for a slab which includes a positive and negative distance from the location and the orientation of the 2D region.

19. The apparatus according to claim 18, wherein the plurality of recorded points include a category which identifies each recorded point by at least one of a biopsy sample location, a seed placement, a drug placement, or a fiducial feature.

20. The apparatus according to claim 19, wherein the selected point includes one or more points selected by category.

21. The apparatus according to claim 18, wherein the recorded points include a relative position from a recognizable point of an organ in the patient.

22. The apparatus according to claim 18, where the indicia includes a transparency indicative of the distance.

23. A method for providing information regarding a relationship between a location of a selected point within a body of a patient and a location and orientation of an ultrasound probe, the method comprising employing a processor to:
receive first information indicating the location and orientation of the ultrasound probe;
determine, based on the first information, second information indicating the location and orientation of a 2D region within the body of the patient scanned by the ultrasound probe;
receive third information indicating the location of the selected point selected from a plurality of recorded points;
determine, based the second and third information, fourth information indicating whether or not the selected point lies within the 2D region;
set location and appearance of indicia on a display based on the fourth information, wherein the appearance of the indicia includes a hue which is a continuous function of three colors;
determine, based on the second information and the third information, fifth information indicating a distance between the selected point and a point within the 2D region which is closest to the selected point; and
control an appearance of the indicia based at least in part on the fifth information, wherein the continuous function of three colors is defined for a slab which includes a positive and negative distance from the location and the orientation of the 2D region.

* * * * *